(12) United States Patent
Iwashita et al.

(10) Patent No.: US 8,625,742 B2
(45) Date of Patent: Jan. 7, 2014

(54) IMAGING SYSTEM AND CONTROL METHOD THEREFOR

(75) Inventors: Atsushi Iwashita, Honjo (JP); Tadao Endo, Honjo (JP); Toshio Kameshima, Kumagaya (JP); Tomoyuki Yagi, Honjo (JP); Katsuro Takenaka, Honjo (JP); Keigo Yokoyama, Honjo (JP); Sho Sato, Kumagaya (JP)

(73) Assignee: Canon Kabushiki Kaisha, Tokyo (JP)

( * ) Notice: Subject to any disclaimer, the term of this patent is extended or adjusted under 35 U.S.C. 154(b) by 294 days.

(21) Appl. No.: 13/107,360

(22) Filed: May 13, 2011

(65) Prior Publication Data

US 2011/0286582 A1    Nov. 24, 2011

(30) Foreign Application Priority Data

May 18, 2010 (WO) .................. PCT/JP2010/058357

(51) Int. Cl.
*H05G 1/54* (2006.01)

(52) U.S. Cl.
USPC .......................................... 378/116; 378/146

(58) Field of Classification Search
USPC ............... 378/42, 62, 91, 114, 115, 116, 146
See application file for complete search history.

(56) References Cited

FOREIGN PATENT DOCUMENTS

| JP | 61-022841 A | 1/1986 |
|---|---|---|
| JP | 3-137589 A | 6/1991 |
| JP | 9-135013 A | 5/1997 |
| JP | 10-332832 A | 12/1998 |
| JP | 11-502357 T | 2/1999 |
| JP | 11-507197 T | 6/1999 |
| JP | 11-318877 A | 11/1999 |
| JP | 3183390 B2 | 7/2001 |
| JP | 2006-280576 A | 10/2006 |
| JP | 2006-346011 A | 12/2006 |
| JP | 4112175 B2 | 7/2008 |
| JP | 4177892 B2 | 11/2008 |
| JP | 4384766 B2 | 12/2009 |

*Primary Examiner* — Jurie Yun
(74) *Attorney, Agent, or Firm* — Canon USA Inc. IP Division

(57) ABSTRACT

An imaging system includes a plurality of imaging apparatuses, each of the imaging apparatuses includes a detector for performing an imaging operation for outputting image data corresponding to applied radiation or light and a controller for controlling the operation of the detector. The imaging apparatuses can independently perform an imaging operation and are movable in accordance with a relative positional relationship thereof. Sensing means obtain information indicative of the relative positional relationship between the imaging apparatuses. A control computer sends a control signal for determining operations of the imaging apparatuses to the controller. The control computer determines the operations of the imaging apparatuses by using the information obtained from the sensing means; and sets an appropriate scanning direction of each of the imaging apparatuses in accordance with the positional relationship thereof.

18 Claims, 10 Drawing Sheets

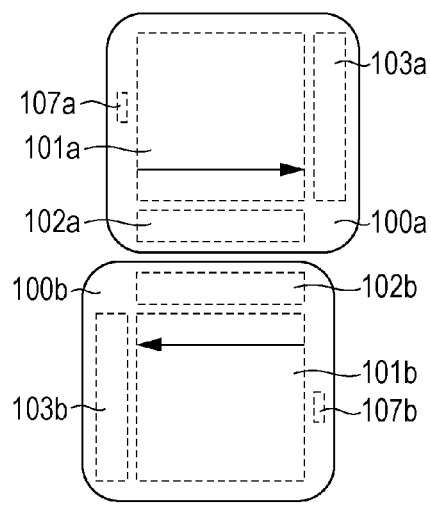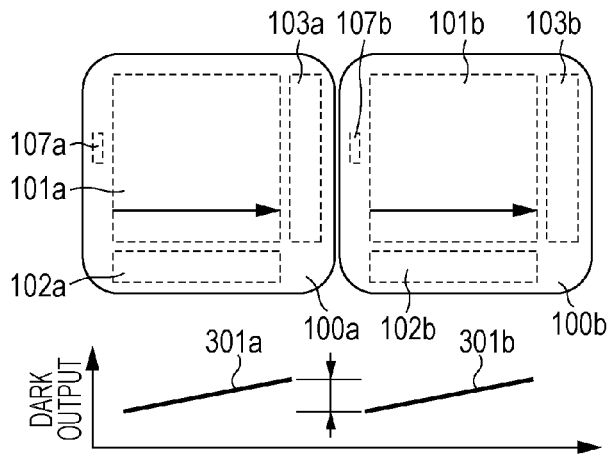
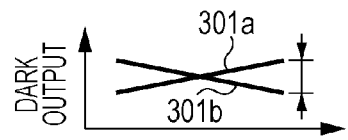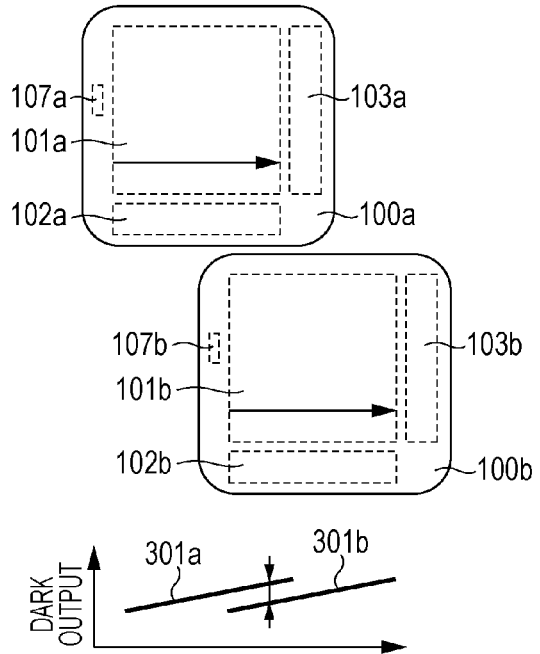
FIG. 3A  FIG. 3B  FIG. 3C

IMAGING SYSTEM AND CONTROL METHOD THEREFOR

TECHNICAL FIELD

The present invention relates to imaging systems and control methods therefor. More particularly, the invention relates to an imaging system used for a radiation imaging system, which is suitably used in medical imaging for still-image radiography, such as radiographic imaging, or for moving-image radiography, such as fluoroscopy, and also relates to a control method for such an imaging system.

BACKGROUND ART

Recently, as imaging apparatuses used for medical imaging or non-destructive inspection using X rays, radiation imaging apparatuses using a flat panel detector (hereinafter referred to as "FPD") have been put into practical use. Certain radiation imaging apparatuses using more than one flat panel detector (i.e., using a plurality of FPDs) have also been proposed. Such imaging apparatuses are used, for example, in the field of medical imaging, as digital imaging apparatuses for still-image radiography, such as radiographic imaging, or for moving-image radiography, such as fluoroscopy.

Concerning radiation imaging apparatuses using a plurality of FPDs, patent literature (PTL) document 1 discloses a photoelectric conversion apparatus including a plurality of substrates (each corresponding to the above-mentioned FPDs) disposed adjacent to each other; each substrate includes a plurality of two-dimensional photoelectric conversion elements. In the photoelectric conversion apparatus described in PTL 1, at least one of scanning circuits and detection circuits are disposed at two opposing sides of the photoelectric conversion apparatus, and the scanning directions of the circuits disposed at the two sides can be set to be the same. In PTL 1, the plurality of FPDs are disposed adjacent to each other in accordance with a predetermined positional relationship.

PTL 2 discloses the use of plural FPDs improve imaging efficiency by using the following technique. A first X-ray tube and a first X-ray detection circuit are used to capture first image data. Additionally, a second X-ray tube and a second X-ray detection circuit are used to capture second image data. Then, the obtained first image data and second image data are subjected to computing processing so as to generate a tomographic image or three-dimensional image of a subject. In PTL 2, the first X-ray detection circuit and the second X-ray detection circuit are disposed perpendicular to each other, such that they cross at right angles with each other in accordance with a predetermined positional relationship.

In the imaging systems using a plurality of FPDs disclosed in the above-described PTL 1 and PTL 2, it is assumed that the FPDs have the same structure or a symmetrical arrangement and are disposed at fixed positions in accordance with a predetermined positional relationship.

However, when constructing an imaging system using a plurality of FPDs which can independently perform an imaging operation (obtaining images) and which can be positioned as desired, the positional relationship of the FPDs is not decided upon in advance. Accordingly, mismatching in the scanning methods among the FPDs, such as inconsistencies in the scanning directions, may occur depending on the positional relationship of the FPDs, which may impair the continuity of a plurality of images obtained from the individual FPDs. Also, if the driving time is different among the plurality of FPDs, mismatching in the scanning methods among the FPDs may also occur, which may impair the continuity of a plurality of images obtained from the individual FPDs. Thus, when a plurality of images obtained from the plurality of FPDs are synthesized, artifacts may occur in the images, which may decrease the image quality.

CITATION LIST

Patent Literature

PTL 1: Japanese Patent Laid-Open No. 9-135013
PTL 2: Japanese Patent Laid-Open No. 2006-346011

SUMMARY OF INVENTION

In order to provide an imaging system that includes a plurality of FPDs which can independently obtain images and which can be positioned as desired and that can prevent the deterioration of the image quality when performing image synthesizing, after being committed to intensive study, the inventor of this application has attained the following various modes of the invention.

An imaging system according to the present invention includes: a plurality of imaging apparatuses, each of which includes a detector for performing an imaging operation for outputting image data corresponding to applied radiation or light and a controller that controls the operation of the detector, each of the imaging apparatuses independently performing an imaging operation and being movable in accordance with a relative positional relationship; sensing means that obtains information indicative of the relative positional relationship of the imaging apparatuses; and a control computer that determines operations of the imaging apparatuses by using the information obtained from the sensing means and that sends a control signal for performing the determined operations to the controller. In a case where the relative positional relationship is a parallel arrangement in which the imaging apparatuses are disposed in parallel with respect to a scanning direction of each of the imaging apparatuses, the control computer determines the operations of the imaging apparatuses so that the scanning direction of each of the imaging apparatuses becomes the same. In a case where the relative positional relationship is a serial arrangement in which the imaging apparatuses are disposed in series with respect to the scanning direction of each of the imaging apparatuses, the control computer determines the operations of the imaging apparatuses so that the scanning direction of each of the imaging apparatuses becomes opposite to each other and so that a time at which scanning is started or ended becomes the same for each of the imaging apparatuses.

A control method according to the present invention is used for an imaging system including a plurality of imaging apparatuses, each of which includes a detector for performing an imaging operation for outputting image data corresponding to applied radiation or light and a controller that controls the operation of the detector, each of the imaging apparatuses independently performing an imaging operation and being movable in accordance with a relative positional relationship thereof. The control method includes: an obtaining step of obtaining information concerning the relative positional relationship of the imaging apparatuses; and a determination step of determining operations of the imaging apparatuses by using the information. In a case where the relative positional relationship is a parallel arrangement in which the imaging apparatuses are disposed in parallel with respect to the scanning direction of each of the imaging apparatuses, the determination step determines the operations of the imaging apparatuses so that the scanning direction of each of the imaging apparatuses becomes the same. In a case where the relative positional relationship is a serial arrangement in which the imaging apparatuses are disposed in series with respect to the scanning direction of each of the imaging apparatuses, the determination step determines the operations of the imaging apparatuses so that the scanning direction of each of the imaging apparatuses becomes opposite to each other and so that a time at which scanning is started or ended becomes the same for each of the imaging apparatuses.

Further features of the present invention will become apparent to persons having ordinary skill in the pertinent art from the following description of exemplary embodiments with reference to the attached drawings.

BRIEF DESCRIPTION OF DRAWINGS

FIGS. 3A, 3B, and 3C are block diagrams illustrating certain factors to be considered in operations of imaging apparatuses according to the present invention.

DESCRIPTION OF EMBODIMENTS

Figure 1A:
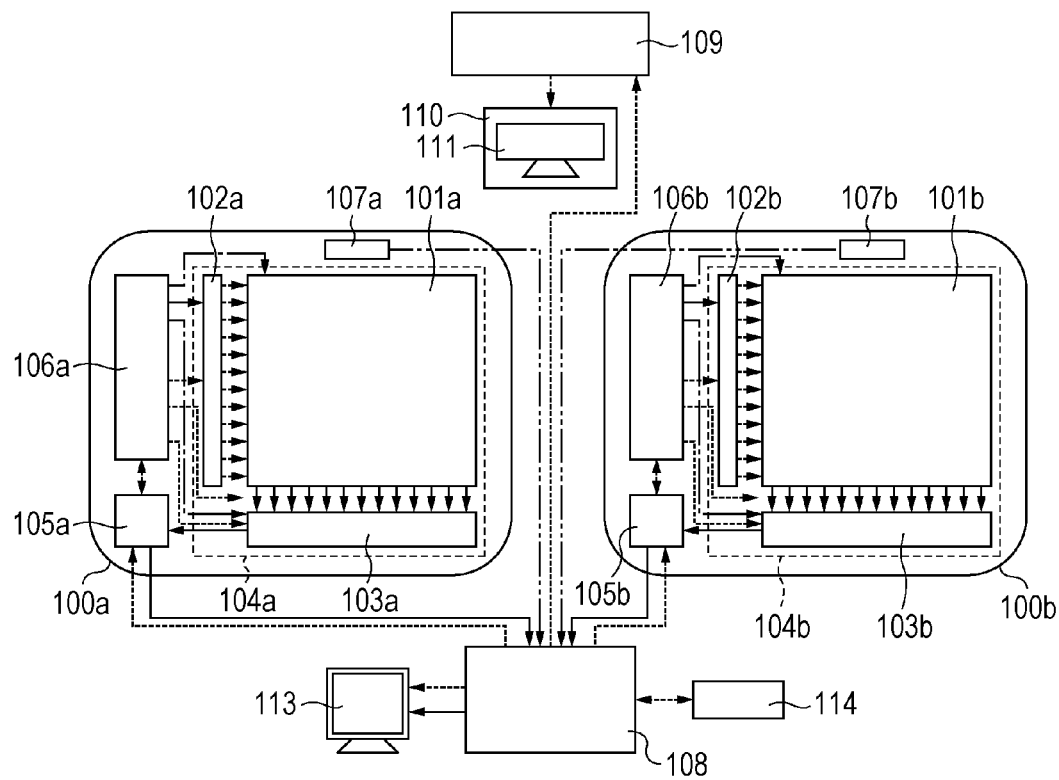
FIGS. 1A and 1B are block diagrams illustrating an imaging system according to a first embodiment of the present invention.

Embodiments to which the present invention can suitably be applied are described in detail below with reference to the drawings.

First Embodiment

An imaging system of this embodiment is first described with reference to FIGS. 1A and 1B. The radiation imaging system of this embodiment includes a radiation generating apparatus 110, a radiation control apparatus 109, a control computer 108, a plurality of imaging apparatuses 100*a* and 100*b*, and sensing units 107*a* and 107*b*, which serve as sensing means for sensing the positional relationship of the plurality of imaging apparatuses 100*a* and 100*b*, respectively. The radiation imaging system of this embodiment also includes a display apparatus 113 and a console 114. In this embodiment, two imaging apparatuses, i.e., a first imaging apparatus 100*a* and a second imaging apparatus 100*b*, are used. Hereafter, elements corresponding to the first imaging apparatus are referred to using the letter "a", while elements corresponding to the second imaging apparatus are referred to using the letter "b" for ease of illustration. However, when describing elements used in common for the first and second imaging apparatuses, these elements are described without using letter denominations and by referring to a generic imaging apparatus. Accordingly, common features of each imaging apparatus (101*a* or 101*b*) can be generally described by referring to a single imaging apparatus 100.

In the present embodiment, an imaging apparatus 100 includes a flat panel detector (FPD) 104, a signal processor 105, and a controller 106. The FPD 104 includes a detection unit 101 including a plurality of pixels for converting radiation or light into an electric signal, a drive circuit 102 for driving the detection unit, and a readout circuit 103 for outputting, as image data, the electric signal from the detection unit driven by the drive circuit 102. The signal processor 105 processes and outputs the image data from the FPD 104. The controller 106 supplies, on the basis of a control signal from the control computer 108, control signals to the individual elements so as to control operations of the FPD. The operations of the FPD include various operation modes, such as a synchronous mode and an asynchronous mode. The controller 106 contains power supply circuits, such as a regulator and an inverter, that receive voltages from an external power supply or a built-in battery, which is not shown, so as to supply voltages necessary for the detection unit 101, the drive circuit 102, and the readout circuit 103. Each imaging apparatus 100 can independently perform an imaging operation (obtaining images) and can be freely disposed at desired positions with respect to a specimen 112, i.e., the imaging apparatus 100 is movable.

The sensing means of the present invention detects the relative positional relationship between the imaging apparatuses 100. In this embodiment, the sensing unit 107 provided for each imaging apparatus 100 corresponds to the sensing means. The sensing unit 107 includes a sensor, a computing unit, communication means, etc., and senses the relative positional relationship between the imaging apparatuses. In this embodiment, each imaging apparatus 100 includes a sensor, a computing unit, and communication means.

The sensor detects the distance between the imaging apparatuses and the directions of movement or orientation of the imaging apparatuses; and the computing unit computes the position and the orientation of the imaging apparatuses, thereby detecting the relative positional relationship between the plurality of imaging apparatuses. As the sensor, an electronic compass, an acceleration sensor (e.g., accelerometer), a distance sensor, or a combination of these or like devices may suitably be used. In this embodiment, each imaging apparatus includes the sensing unit 107. However, the present invention is not restricted to this, and it is sufficient that the imaging system includes sensing means for sensing and determining the relative positional relationship between the imaging apparatuses. Accordingly, the sensing means can be incorporated within the imaging apparatus or can be provided separately from the imaging apparatus.

As an example in which sensing means are provided separately from the imaging apparatus 100, each imaging apparatus 100 is attached to a holding mechanism, such as an arm, and a sensing unit, such as an encoder, is provided for the holding mechanism, so as to detect the length, the angle, etc, of the imaging apparatus. The holding mechanism may have a system that is passively moved by an external force, or may include an actuator and have a system that is actively moved.

Each imaging apparatus may be provided with a sensor and communication means, and the control computer 108, which is discussed later, may be provided with a computing unit, in which case, the sensor, the communication means, and the computing unit may form the sensing means. The computing unit of the sensing means determines, on the basis of arrangement information concerning each imaging apparatus, the relative positional relationship between the imaging apparatuses in the common coordinate system by performing computing processing. The arrangement information includes information for transforming the coordinate system of the FPD into the common coordinate system, or information for transforming the common coordinate system into the coordinate system of the FPD. For example, the arrangement information includes information concerning a specific pixel of the FPD, information concerning a first side of the detection unit on which the drive circuit is disposed and a second side of the detection unit on which the read-out circuit is disposed, information concerning the plane of incidence of the FPD on which radiation or light is incident, and information concerning the scales of the first side and the second side.

Figure 2:
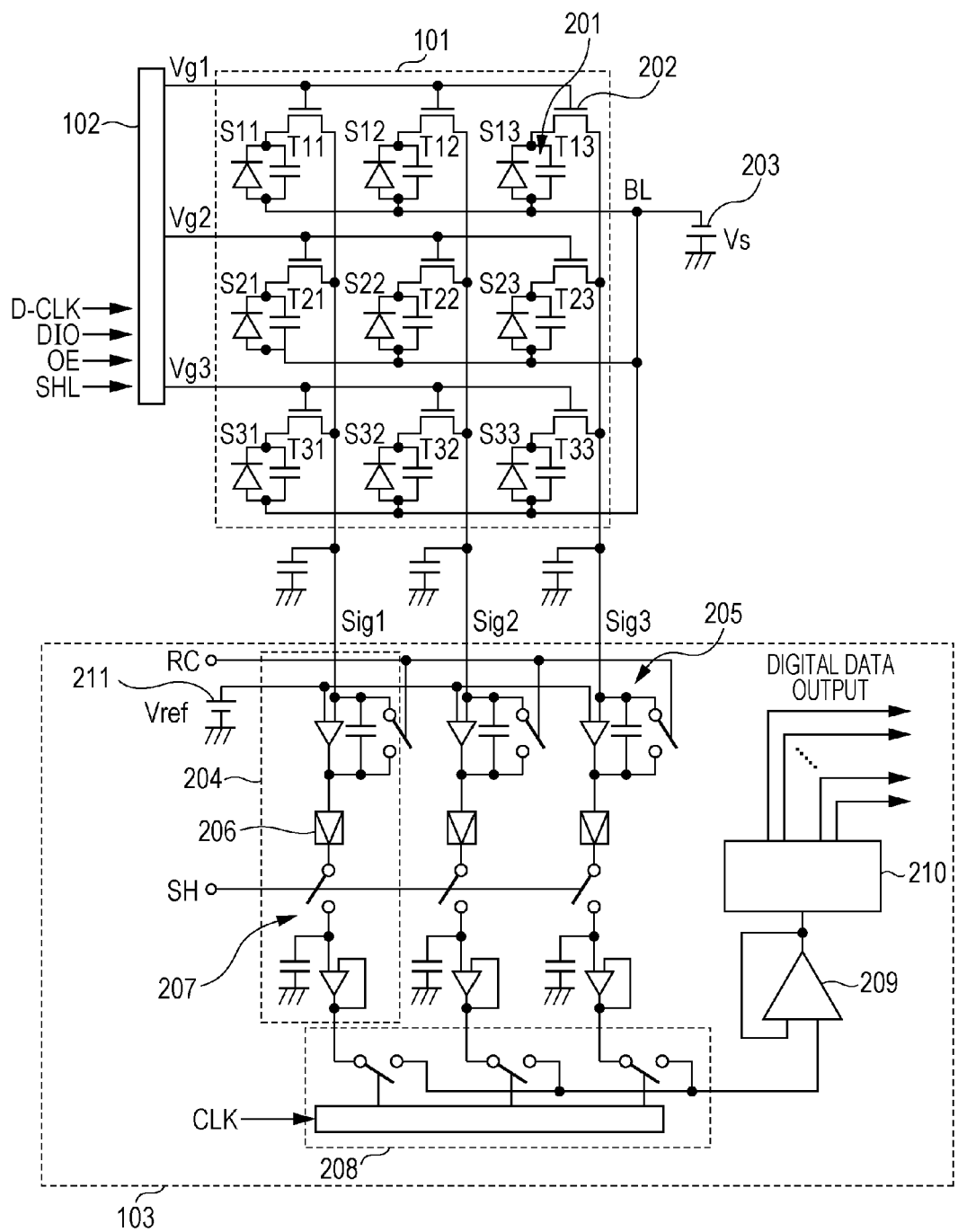
FIG. 2 is an equivalent circuit diagram illustrating an imaging apparatus according to the present invention.

In this embodiment, the specific pixel of the FPD is the pixel positioned at the intersection at which the first side and the second side cross each other, and corresponds to, for example, in FIG. 2, the pixel positioned at the intersection of the third row and the first column. The information concerning the specific pixel is information concerning the position at which the specific pixel is disposed within the detection unit with respect to the drive circuit and the read-out circuit. In the above-described example, assuming that, in the coordinate system of the FPD, the first side is the Y axis and the second side is the X axis, the information concerning the specific pixel indicates that the relative position of the specific pixel with respect to the drive circuit and the read-out circuit is the origin. Additionally, in the above-described example, the information concerning the first side indicates that the first side is the Y axis of the first quadrant having the specific pixel as the origin, and the information concerning the second side indicates that the second side is the X axis of the first quadrant having the specific pixel as the origin. Further, in the above-described example, the information concerning the scales of the first side and the second side is information defined by the pitch of the pixels within the detection unit. In this embodiment, the sensing unit 107, which serves as the sensing means, is disposed in the imaging apparatus by being integrally formed with the FPD. Thus, the coordinate system of the FPD is transformed into the common coordinate system by using the information concerning the specific pixel of the FPD, the information concerning the first side and the second side, the information concerning the plane of incidence, and the information concerning the scales, as viewed from the sensing unit 107. The arrangement information may also include information concerning the direction of one imaging apparatus as viewed from the other imaging apparatus.

The control computer 108 synchronizes the radiation generating apparatus 110 with each imaging apparatus 100, sends a control signal for determining the operation of each imaging apparatus 100, and performs image processing for correcting, storing, and displaying image data supplied from each imaging apparatus 100. The control computer 108 also obtains information concerning the relative positional relationship between the imaging apparatuses from the sensing means. On the basis of this information, the control computer 108 determines the operation of each imaging apparatus so that the discontinuity between image data obtained from the imaging apparatuses becomes smaller than that when each imaging apparatus independently performs an imaging operation. The operation of each imaging apparatus determined by the control computer 108 is described in detail later. On the basis of this information, the control computer 108 determines a suitable scanning operation performed by each imaging apparatus. Alternatively, a radiographer may specify the operation of each imaging apparatus via the console 114. The control computer 108 sends a control signal based on the operation of each imaging apparatus determined by the controller of each imaging apparatus, and also sends a control signal based on an exposure request input from the console 114 to the radiation control apparatus 109.

The radiation control apparatus 109 receives a control signal from the control computer 108 so as to control an operation for emitting radiation from a radiation source 111 contained in the radiation generating apparatus 110. The console 114 inputs information concerning a specimen and radiography conditions, as parameters used for the control computer 108 to perform various control operations, and transmits the information to the control computer 108. The display apparatus 113 displays image data subjected to image processing in the control computer 108.

The FPD applied to the imaging apparatus according to the present invention is described below with reference to FIG. 2. The same elements as shown in FIGS. 1A and 1B are designated by like reference numerals, and a detailed explanation thereof is omitted. In FIG. 2, for simple description, the FPD having pixels arranged in a matrix of 3 rows and 3 columns is shown. However, an actual imaging apparatus has a larger number of pixels, for example, a 17-inch imaging apparatus has pixels arranged in a matrix of about 2800 rows and 2800 columns.

Therefore, as illustrated in FIG. 2, the detection unit 101 has a plurality of pixels disposed in a matrix form. Each pixel includes a conversion element 201 that converts radiation or light into electric charge, and a switch element 202 that outputs an electric signal corresponding to the electric charge. In this embodiment, as a photoelectric conversion element for converting light applied to the conversion element into electric charge, a positive-intrinsic-negative (PIN) photodiode having amorphous silicon as the major material and disposed on an insulating substrate, such as a glass substrate, is used. However, a metal-insulator-semiconductor (MIS) sensor may be used. Also, as the conversion element, an indirect conversion element provided with a wavelength converter on a radiation incident side of the above-described photoelectric conversion element is suitably used. That is, the wavelength converter provided for the indirect conversion element converts radiation into light having a wavelength band that can be sensed by the photoelectric conversion element. Alternatively, as the conversion element, a direct conversion element for directly converting radiation into electric charge may suitably be used. As the switch element 202, a transistor having a control terminal and two main terminals is suitably used, and in this embodiment, a thin-film transistor (TFT) is used. The conversion element 201 is electrically connected at one electrode to one of the main terminals of the switch element 202, and is electrically connected at the other electrode to a bias power supply 203 via a bias line (BL), which is used in common for all of the conversion elements 201. The control terminals of a plurality of switch elements in the row direction, for example, T11 through T13, are all electrically connected to a first drive line Vg1. A drive signal for controlling the conductive state of the switch elements for each row is supplied from the drive circuit 102 to the switch elements in the same row via a drive line. The other main terminals of a plurality of switch elements in the column direction, for example, T11 through T31, are electrically connected to a first signal line Sig1. The switch elements T11 through T13 output an electric signal corresponding to the electric charge of the conversion elements to the readout circuit 103 via the signal line while they are in the conductive state. A plurality of signal lines Sg1 through Sg3 arranged in the column direction send, in parallel, electric signals output from the plurality of pixels to the readout circuit 103.

In the readout circuit 103, amplifier circuits 204 that amplify electric signals output in parallel from the detection unit 101 are provided for the individual signal lines. Each amplifier circuit 204 includes an integrating amplifier 205 that amplifies an output electric signal, a variable amplifier 206 that amplifies an electric signal output from the integrating amplifier 205, and a sample and hold circuit 207 that samples and holds an amplified electric signal. The integrating amplifier 205 includes an operational amplifier that amplifies and outputs a read electric signal, an integral capacitor, and a reset switch. The operational amplifier, the integral capacitor and the reset switch are not labeled, but are clearly shown as being part of integrating amplifier 205. The integrating amplifier 205 can vary the amplification factor by changing the value of the integral capacitor. In the operational amplifier, an output electric signal is input into the inverting input terminal, and a reference voltage Vref is input into the non-inverting input terminal from a reference power supply 211, and an amplified electric signal is output from the output terminal. The integral capacitor is disposed between the inverting input terminal and the output terminal of the operational amplifier. The sample and hold circuit 207 is provided for each amplifier circuit, and includes a sampling switch and a sampling capacitor. The readout circuit 103 also includes a multiplexer 208 that sequentially outputs electric signals read in parallel from the individual amplifier circuits 204 as a serial image signal, and a buffer amplifier 209 that performs impedance conversion on the image signal and outputs the converted image signal. An image signal Vout, which is an analog electric signal, output from the buffer amplifier 209 is converted into digital image data by an A/D converter 210, and is output to the control computer 108 via the signal processor 105 shown in FIG. 1A.

The controller 106 shown in FIG. 1A includes the bias power supply 203 and the reference power supply 211 of the amplifier circuits shown in FIG. 2. The bias power supply 203 supplies a biasing voltage Vs to all the other electrodes of the conversion elements via the bias line BL. The reference power supply 211 supplies the reference voltage Vref to the non-inverting input terminals of the individual operational amplifiers.

The drive circuit 102 outputs a drive signal to each drive line in accordance with control signals (D-CLK, OE, DIO, and SHL) received from the controller 106 shown in FIG. 1A. The drive signal includes a conducting voltage Vcom that makes the switch elements be in the conductive state and a non-conducting voltage Vss that makes the switch elements be in the non-conductive state. With this arrangement, the drive circuit 102 controls the switch elements to be in the conductive state or in the non-conductive state so as to drive the detection unit 101. The control signal D-CLK is a shift clock of a shift register which is used as the drive circuit, the control signal DIO is a pulse transferred by the shift register, and the control signal OE is a signal for controlling the output terminal of the shift register. The control signal SHL is a signal for selecting the shifting direction (scanning direction) of the drive circuit. If the control signal SHL is at a high level, the scanning direction is a direction from the drive line Vg1 to Vg3. If the control signal SHL is at a low level, the scanning direction is a direction from the drive line Vg3 to Vg1. With this arrangement, the time necessary for driving the detection unit and the scanning direction indicating the order in which the drive circuit 102, which can set the scanning direction to be either of the above-described two directions, supplies a drive signal to the drive lines are set. Also, the controller 106 supplies a control signal RC, a control signal SH, and a control signal CLK to the readout circuit 103 so as to control the operations of the individual elements of the readout circuit 103. The control signal RC controls the operation of the reset switch of the integrating amplifier, the control signal SH controls the operation of the sample and hold circuit 207, and the control signal CLK controls the operation of the multiplexer 208.

The concept for determining the operations of each imaging apparatus of the present invention is described below with reference to FIGS. 3A through 5. For simple description, in FIGS. 3A through 4E, two imaging apparatuses are used by way of example. However, the invention of the present application is not restricted to the use of two imaging apparatuses, and can be suitably applied to the use of three or more imaging apparatuses.

A description is first given, with reference to FIGS. 3A through 3C, of the discontinuity between image data obtained from individual imaging apparatuses, which is a factor to be considered in the operation of the imaging apparatuses of the present invention. When two imaging apparatuses 100 are disposed on the same plane, the following positional relationships between the two imaging apparatuses 100 can be considered: a parallel arrangement in which the imaging apparatuses are disposed in parallel with respect to the scanning direction, as shown in FIG. 3A; a serial arrangement in which the imaging apparatuses are disposed in series with respect to the scanning direction, as shown in FIG. 3B; and a parallel/displacement arrangement in which the imaging apparatuses are disposed in parallel with respect to the scanning direction and are displaced from each other in the scanning direction, as shown in FIG. 3C.

In the parallel arrangement of FIG. 3A, the scanning directions of the two imaging apparatuses may be opposite to each other. A dark output 301 contained in the output from each imaging apparatus is characterized by varying in accordance with the scanning of the imaging apparatus. Due to this variation in the characteristics of the dark output 301, shading occurs in the output image data. This variation characteristic of the dark output is also influenced by a period from which an application of a biasing voltage to the conversion elements of the imaging apparatus is started until image data is output. Accordingly, even if correction is made by using dark output image data that is separately obtained from actual image data, the problem of shading may still remain since the time at which the dark output image data is obtained is different from the time at which the actual image data is obtained. If the scanning directions of the two imaging apparatuses disposed in parallel are opposite to each other, the variation characteristics of the dark outputs become opposite between the two imaging apparatuses, whereby a large difference in the characteristics of the dark outputs is generated between some adjacent pixels of the two imaging apparatuses. This may give rise to image discontinuity in the image data output from the two imaging apparatuses.

Also, in the serial arrangement of FIG. 3B, the scanning directions of the two imaging apparatuses may be the same. In this case, since the variation characteristics of the dark outputs are the same for the two imaging apparatuses, a large difference in the characteristics of the dark outputs is generated between some adjacent pixels of the two imaging apparatuses. This may cause image discontinuity in the image data output from the two imaging apparatuses.

Further, in the parallel/displacement arrangement of FIG. 3C in which the two imaging apparatus are disposed in parallel with respect to the scanning direction and are displaced from each other in the scanning direction, the detection unit of one imaging apparatus may partially overlap with that of the other imaging apparatus in the direction parallel to the drive lines. In this case, if the time at which the scanning of one imaging apparatus is the same as that of the other imaging apparatus, a large difference in the characteristics of the dark outputs is generated between some adjacent pixels in the partially overlapped region of the two imaging apparatuses. This may cause image discontinuity in the image data output from the two imaging apparatuses.

In view of the foregoing situations, at least one embodiment of the present invention is directed to a novel operation control performed by the control computer 108 for each imaging apparatus, which can reduce the possibility of the above-described image discontinuity occurring. The operation control performed by the control computer 108 is described below with reference to FIGS. 4A through 5.

Figure 4A:
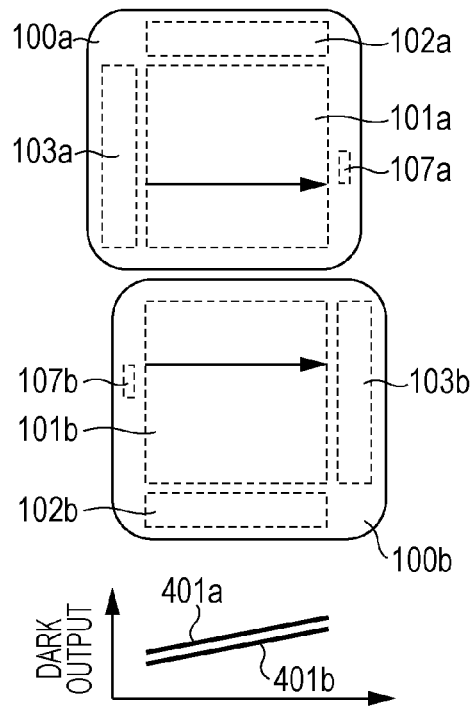
FIGS. 4A through 4E are block diagrams illustrating certain operation controls performed by an imaging system according to the present invention.
Figure 4B:
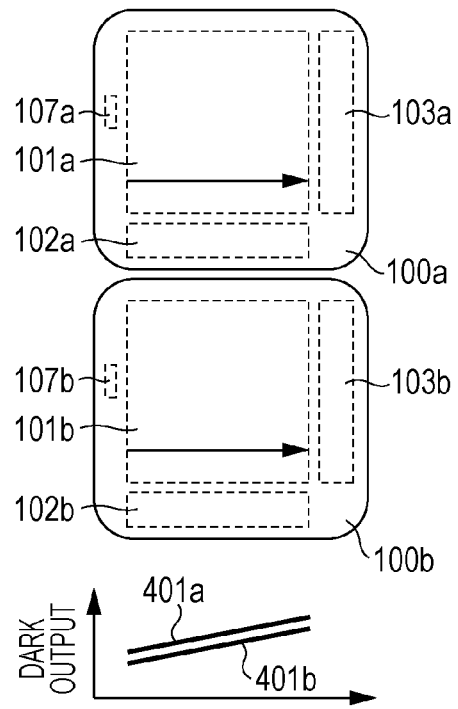

In the case of the parallel arrangement, as shown in FIGS. 4A and 4B, it is desired that the operation of each of the two imaging apparatuses disposed in parallel be controlled so that the scanning directions of the two imaging apparatuses become the same. With this arrangement, the variation characteristics of the dark outputs become the same for the two imaging apparatuses. It is thus possible to prevent the generation of a large difference in the characteristics of the dark outputs between some adjacent pixels of the two imaging apparatuses. This can reduce the possibility of image discontinuity occurring in the image data output from the two imaging apparatuses.

Figure 4C:
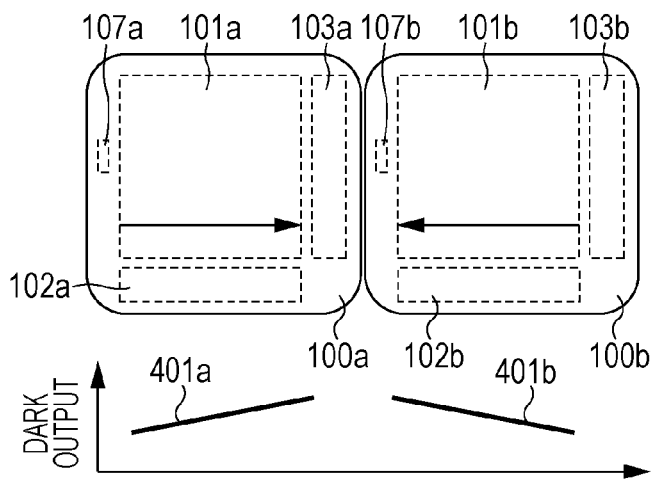
Figure 4D:
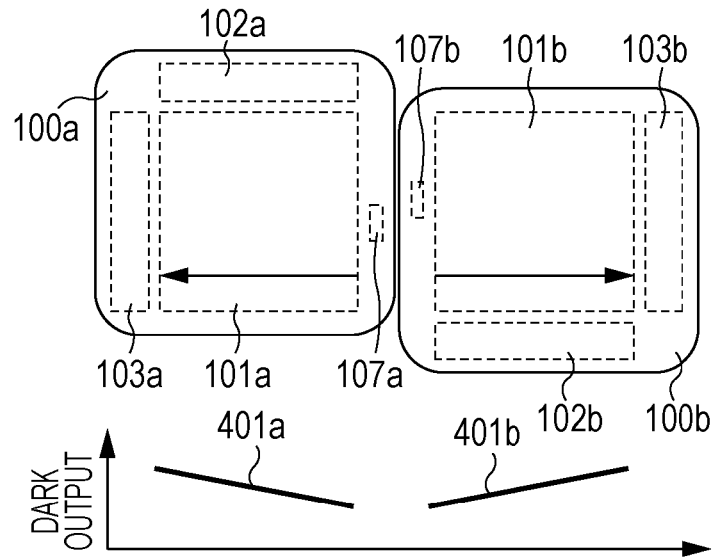

In the case of the serial arrangement, as shown in FIGS. 4C and 4D, it is desired that the operation of each of the two imaging apparatuses disposed in series be controlled so that the scanning directions of the two imaging apparatuses become opposite and so that the time at which the scanning of one imaging apparatus is started or ended becomes substantially the same as that of the other imaging apparatus. With this arrangement, since the time at which the scanning of pixels of one imaging apparatus adjacent to the corresponding pixels of the other imaging apparatus is started or ended is substantially the same as that of the other imaging apparatus, the characteristics of the dark outputs become substantially the same for the two imaging apparatuses. It is thus possible to prevent the generation of a large difference in the characteristics of the dark outputs between some adjacent pixels of the two imaging apparatuses. This can reduce the possibility of image discontinuity occurring in the image data output from the two imaging apparatuses.

Figure 4E:
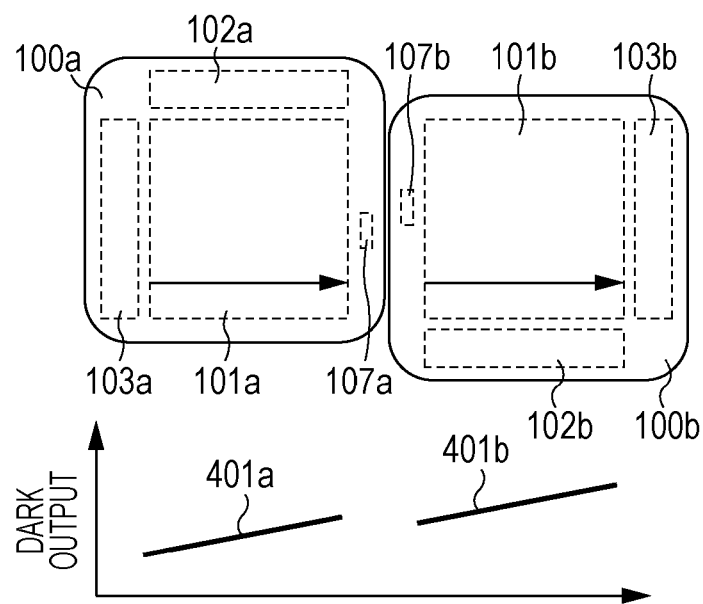

In this case, the operation of each imaging apparatus may also be controlled, as shown in FIG. 4E, so that the scanning directions of the two imaging apparatuses become the same and so that the time at which the scanning of one imaging apparatus, which is first scanned, is ended is substantially the same as the time at which the scanning of the other imaging apparatus, which is subsequently scanned, is started. With this arrangement, since the storage time for adjacent pixels between the two imaging apparatuses becomes substantially the same, the characteristics of the dark outputs approximate to each other. In this control, however, the entire time necessary for the scanning of the imaging apparatuses is longer than the cases shown in FIGS. 4C and 4D, and accordingly, the radiography time and the time before an image is displayed become longer than those of the cases shown in FIGS. 4C and 4D.

Figure 5:
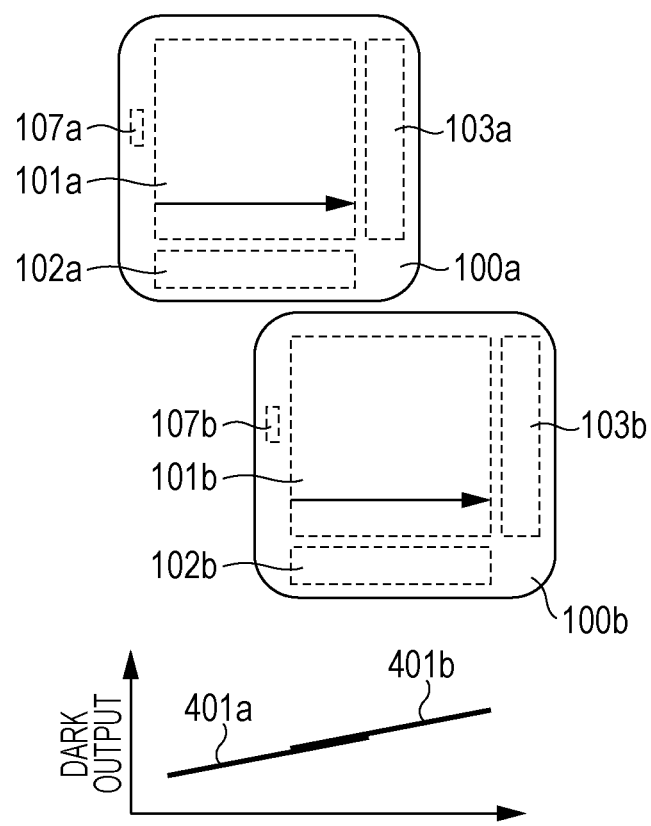
FIG. 5 is a block diagram illustrating an operation control performed by an imaging system according to the present invention.

In the case of the parallel/displacement arrangement in which the two imaging apparatuses are disposed in parallel with respect to the scanning direction and are displaced from each other in the scanning direction, as shown in FIG. 5, the scanning directions of the two imaging apparatuses are controlled to be the same. Additionally, the time at which the scanning of each imaging apparatus is started is controlled so that pixels adjacent to each other in the partially overlapped region of the detection units in the scanning direction between the imaging apparatuses are scanned substantially at the same time. With this arrangement, the characteristics of the dark outputs between the adjacent pixels in the partially overlapped region between the two imaging apparatuses approximate to each other. It is thus possible to prevent the generation of a large difference in the characteristics of the dark outputs between some adjacent pixels of the two imaging apparatuses. This can reduce the possibility of image discontinuity occurring in the image data output from the two imaging apparatuses.

If the difference in the characteristics of the dark outputs between adjacent pixels of the two imaging apparatuses is equal to or lower than a predetermined allowed threshold, image discontinuity cannot be recognized in the image data. Thus, the image data obtained from the two imaging apparatuses can be used. If the difference in the characteristics of the dark outputs is buried in the random noise of the FPD of at least one imaging apparatus, it cannot be recognized as image discontinuity in the image data. Accordingly, the predetermined allowed threshold is desirably equal to or lower than a level at which the difference in the characteristics of the dark outputs is buried in the random noise of the FPD of at least one imaging apparatus. More specifically, in fluoroscopy, the predetermined allowed threshold is desirably equal to or lower than twice the magnitude of the random noise of the FPD of at least one imaging apparatus, and in radiographic imaging, the predetermined allowed threshold is desirably equal to or lower than the random noise of the FPD of at least one imaging apparatus. Thus, in fluoroscopy, the control computer 108 determines and controls the operation of each imaging apparatus so that the difference in the dark outputs between the adjacent pixels of the imaging apparatuses becomes equal to or lower than the twice the magnitude of the random noise. Also, in radiographic imaging, the control computer 108 determines and controls the operation of each imaging apparatus so that the difference in the dark outputs between the adjacent pixels of the imaging apparatuses becomes equal to or lower than the random noise. More preferably, the control computer 108 determines and controls the operation of each imaging apparatus by using information concerning the relative positional relationship of the imaging apparatuses obtained from the sensing means so that the difference in the dark outputs between the adjacent pixels of the imaging apparatuses is minimized. It is thus possible to prevent the generation of a large difference in the characteristics of the dark outputs between adjacent pixels of the two imaging apparatuses. This can reduce the possibility of image discontinuity occurring in the image data output from the two imaging apparatuses.

If two or more imaging apparatuses are disposed, the scanning direction and/or the time at which the scanning is started are/is determined according to the above-described concept. Also, image processing using information concerning the relative positional relationship may be performed on the obtained image data. For example, processing for shifting, inverting, or rotating image data can suitably be performed so that the image data can be adjusted to the position and the direction in the common coordinate system.

The operation of the imaging apparatus and the imaging system according to the present invention is described below with reference to the flowchart shown in FIG. 6A. The control computer 108 shown in FIGS. 1A and 1B has an asynchronous mode in which a plurality of imaging apparatuses are controlled to be independently operated and a synchronous mode in which a plurality of imaging apparatuses are controlled to be operated in synchronization with each other. As the imaging operation, either of still-image radiography (radiographic imaging) or moving-image radiography (fluoroscopy) may be performed. Also, during the imaging operation, the asynchronous mode and the synchronous mode may be switched, or the still-image radiography or the moving-image radiography may be switched. If the mode or the type of radiography is switched, an instruction to change the drive mode is sent to the drive unit of each imaging apparatus.

Figure 6A:
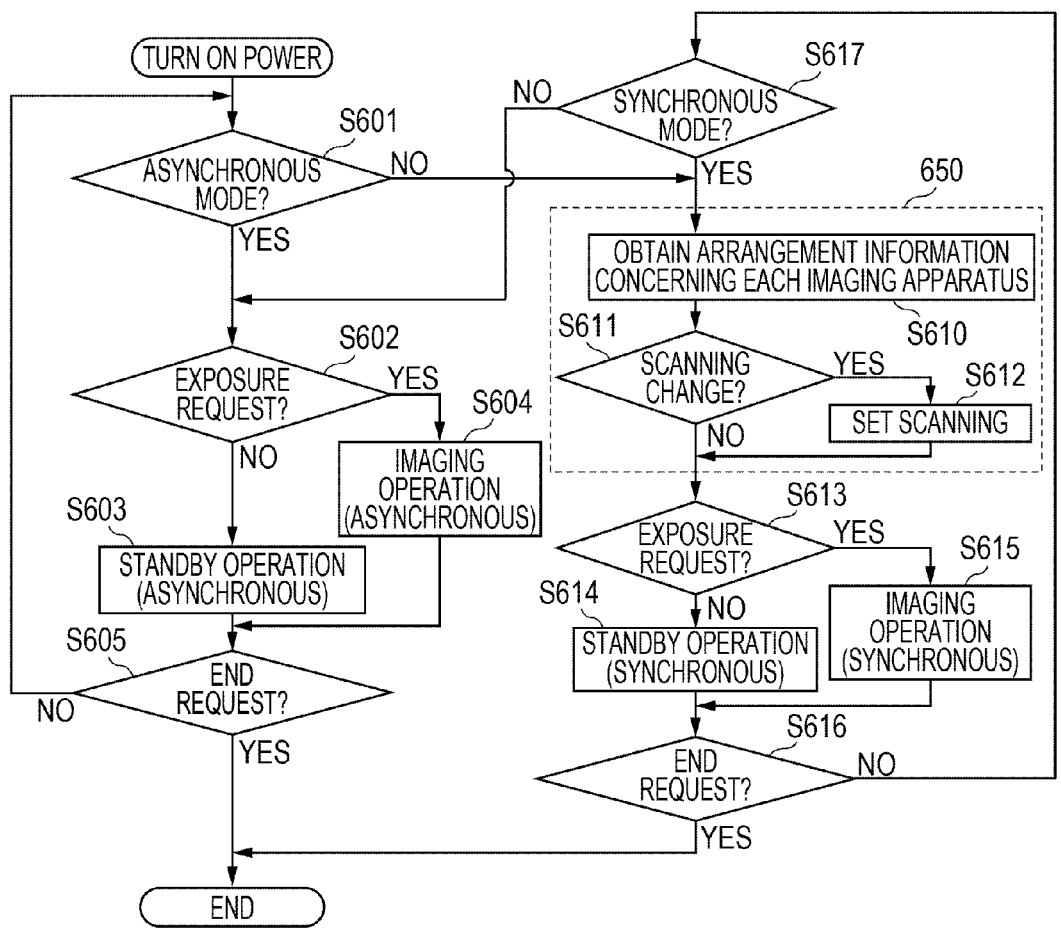
FIGS. 6A and 6B are flowcharts illustrating process steps of operation controls performed by an imaging system according to the present invention.

In FIG. 6A, after the imaging system is powered ON, control computer 108 determines whether the system should perform imaging in the synchronous or asynchronous mode (S601). In the asynchronous mode (YES in S601), control computer 108 determines at S602 whether an exposure request is received (e.g., initiated by an operator), if there is no radiation exposure request (NO in S602), an instruction to perform an asynchronous standby operation (S603) is sent to the drive control unit of each imaging apparatus. The standby operation is the following initializing operation. The drive circuit 102 scans the drive lines according to at least one of the scanning methods, i.e., scanning the drive lines progressively line by line, scanning the drive lines at one time, or scanning the drive lines in units of several lines, so as to initialize the conversion elements 201. This initializing operation is performed once or is repeatedly performed a plurality of times. If there is an exposure request (YES at S602), an instruction to perform an asynchronous imaging operation (S604) is sent to the drive control unit of at least one of the imaging apparatuses. The imaging operation is the operation for outputting image data from the imaging apparatus 100. This imaging operation includes a storage operation and an output operation. In the storage operation, the switch element of each pixel is placed in the non-conductive state during a predetermined period including the period during which radiation or light is applied to the conversion elements. In the output operation, the drive lines are scanned line by line or in units of a plurality of lines so that the electric charge generated in the conversion elements during the storage operation is output. After (or during) the imaging operation, if there is an end request (YES at S605), the operation ends. If there is no end request (NO at S605), the flow returns to S601 to determine the mode.

Referring back to S601, in the synchronous mode (NO at S601), the imaging system enters the operation routine 650 of the portion of FIG. 6A surrounded by the broken lines. In this operation routine, the control computer 108 determines the suitable scanning for each imaging apparatus in accordance with the above-described control method on the basis of information concerning the relative positional relationship (arrangement) of the imaging apparatuses received from the sensing means shown in FIGS. 1A and 1B. The determined scanning may be displayed on the display apparatus 113, and a user may determine the scanning based on the determined scanning or arrangement. That is, at S610, the control computer 108 obtains arrangement information corresponding to each imaging apparatus and determines the appropriate scanning based on the arrangement information. If it is necessary to change the scanning (YES at S611), the control computer sends an instruction to change the scanning to the drive unit of each imaging apparatus. In other words, the control computer sets the type of scanning (S612). In the case of moving-image radiography, the scanning may be changed for each frame. If there is no need for a change in the scanning, the control computer determines whether an exposure request is received (S613). If there is no radiation exposure request (NO at S613), the control computer sends an instruction to perform a standby operation in synchronization with the other imaging apparatuses to the controller of each imaging apparatus (S614). If there is an exposure request (YES at S613), the control computer sends an instruction to perform an imaging operation in synchronization with the other imaging apparatuses to the controller of each imaging apparatus (S615). If there is an end request (YES at S616), the operation ends. If there is no end request (NO at S616), the control computer determines whether the operation should continue in the synchronous mode (YES at S617) or switch to the asynchronous mode (NO at S617).

Another control operation performed by a radiation imaging system according to the present invention is described below with reference to the flowchart shown in FIG. 6B. This flowchart shows another example of the operation routine 650 of the portion surrounded by the broken lines in the flowchart shown in FIG. 6A, i.e., another example of the block that obtains arrangement information concerning each imaging apparatus and another example of the block that determines whether the scanning is changed.

Figure 1B:
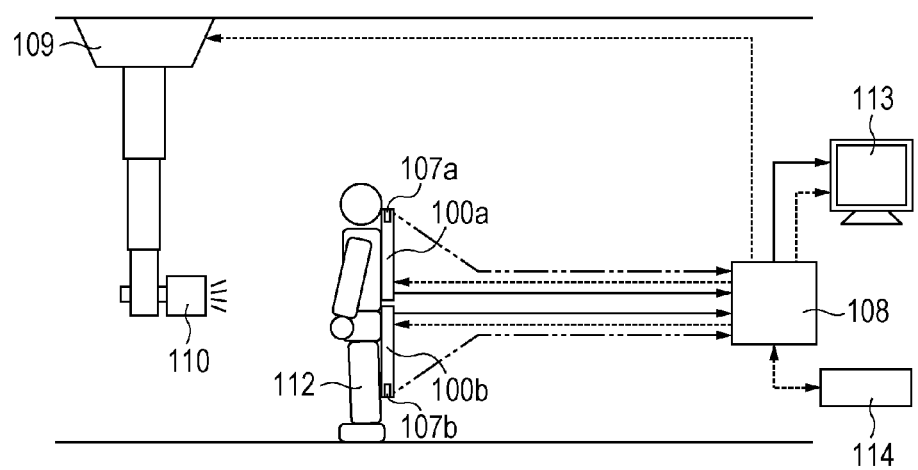
Figure 6B:
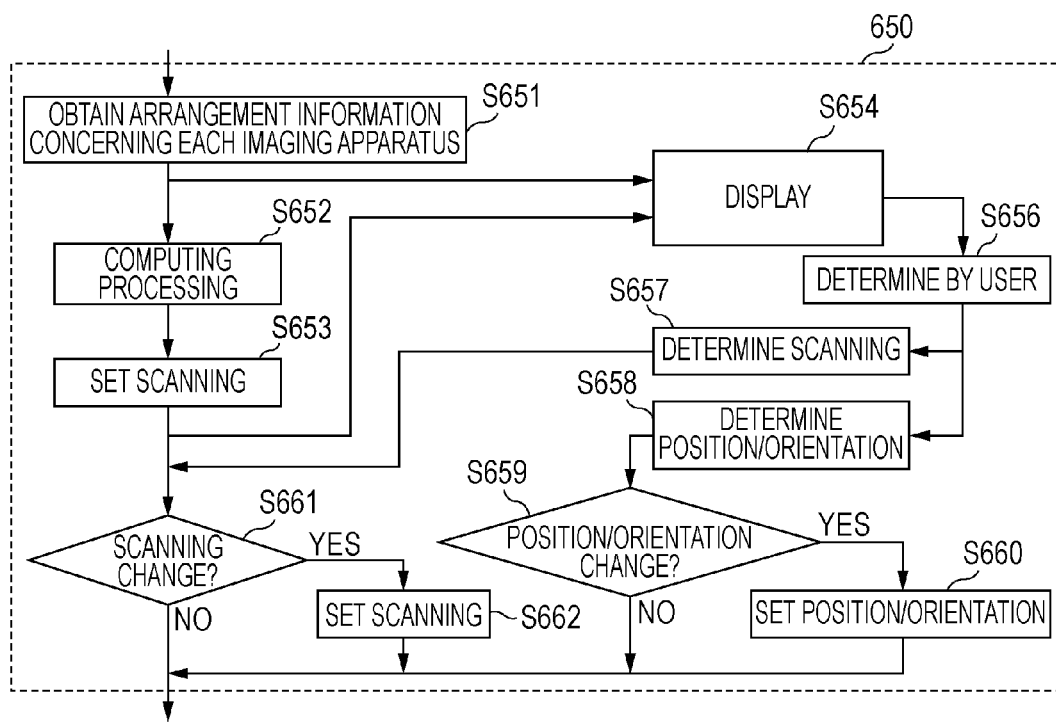

In FIG. 6B, upon entering the operation routine 650, the control computer obtains arrangement information for each imaging apparatus (S651) and determines suitable scanning for each imaging apparatus (S652) in accordance with the above-described control method on the basis of information concerning the relative positional relationship of the imaging apparatuses received from the sensing means shown in FIGS. 1A and 1B. The control computer can set the scanning (S653), and also displays for the user (S654) the relationship of the arrangement between the imaging apparatuses and suitable scanning on the display apparatus 113. If the arrangement of the imaging apparatuses is not suitable for correct imaging to a degree that can increase image discontinuity (instead of minimizing such discontinuity), information for warning of this potentially negative effect may be displayed. On the basis of the information displayed, the user may determine (S656) to re-specify the scanning method or accept the scanning set by the computer (S657). Additionally, if the radiation imaging system includes a mechanism for holding the imaging apparatuses (not shown) and a function for driving the mechanism (not shown), the user may correct the positions or the orientations of the imaging apparatuses (S658). In this case, the control computer determines (S659) the suitable operations of the imaging apparatuses and the suitable positions to which the imaging apparatuses are moved by using the arrangement information concerning each imaging apparatus, and displays the determined result for the user. Upon determining that the operations and the positions proposed by the user are acceptable (YES at S659), the control computer moves each imaging apparatus to the position or the orientation specified by the user by using the mechanism for holding the imaging apparatuses and the function for driving the mechanism. Thus, the control computer sets the position and orientation of each imaging apparatus (S660) based on arrangement information determined by the user. On the other hand, after the user chooses to change or accept the scanning in step S657, control computer determines whether to change (S661) and set the scanning (S662) in the same manner as described in steps S611 and S612.

Second Embodiment

Figure 7:
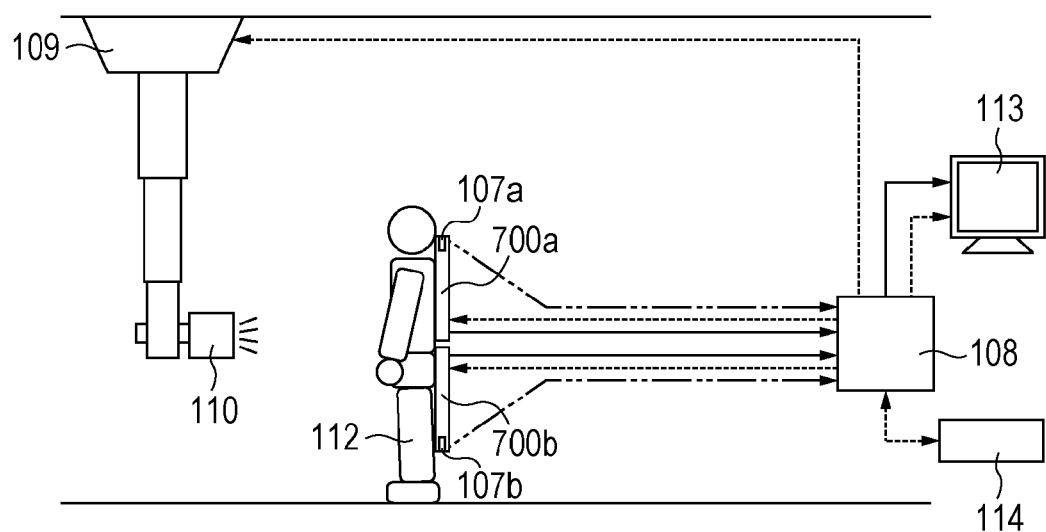
FIG. 7 is a block diagram illustrating an imaging system according to a second embodiment of the present invention.

An imaging apparatus according to a second embodiment of the present invention is described below with reference to FIG. 7. Elements having the same configuration as those of the first embodiment are designated by like reference numerals, and a detailed description thereof is omitted.

In the first embodiment, it is assumed that the plurality of imaging apparatuses are the same type and the plurality of FPDs are the same type. In this embodiment, however, different types of FPDs are used. The following cases are now considered. In one case, an imaging apparatus 700a shown in FIG. 7 uses an FPD(A) which is the same as the FPD 104 of the imaging apparatus 100a shown in FIGS. 1A through 2, while an imaging apparatus 700b uses an FPD(B) which is the same as the FPD 104 in the pixel pitch and is different from the FPD 104 in the number of pixels. More specifically, the FPD(B) has a larger number of rows of pixels forming the detection unit than the FPD(A). In this case, it is now assumed that, when each imaging apparatus is allowed to independently perform an imaging operation, the scanning time for obtaining one image from each imaging apparatus is the same, and that the imaging apparatuses are disposed in parallel. In another case, the imaging apparatus 700a uses the FPD(A) which is the same as the FPD 104 of the imaging apparatus 100a shown in FIGS. 1A through 2, while the imaging apparatus 700b uses the FPD(B) which is the same as the FPD 104 in the number of pixels and is different from the FPD 104 in the pixel pitch. In this case, it is now assumed that the scanning time for obtaining one image from each imaging apparatus is the same and that the imaging apparatuses are disposed in parallel. In still another case, although both the imaging apparatuses 700a and 700b use the same FPDs, the scanning time for obtaining one image from the imaging apparatus 700b is different from that from the imaging apparatus 700a, and the imaging apparatuses are disposed in parallel. In yet another case, the FPD of an imaging apparatus is different from the FPD of the other imaging apparatus in the pixel pitch, the number of pixels, and the scanning time for obtaining one image. The imaging apparatuses are disposed in parallel. In the above-described cases, a large difference in the characteristics of the dark outputs is generated between adjacent pixels of the two imaging apparatuses. This may cause image discontinuity in image data output from the two imaging apparatuses.

Accordingly, the inventor of the present application has designed a novel operation control performed by the control computer 108 for each imaging apparatus, which can reduce the possibility of the above-described image discontinuity occurring. As in the first embodiment, the control computer 108 controls the operation of each imaging apparatus so that the scanning directions of the two imaging apparatuses disposed in parallel become the same. Additionally, the control computer 108 controls the operation of each imaging apparatus so that the pixels most adjacent to each other between the two imaging apparatuses are scanned at the same time. For example, if two imaging apparatuses are disposed in parallel, and if the FPD(A) of one imaging apparatus is the same as the FPD(B) of the other imaging apparatus in the pixel pitch and is different from the FPD(B) in the number of pixels, the frequency of the control clock D-CLK of the shift register contained in the drive circuit of one imaging apparatus is controlled to the same as that of the other imaging apparatus. It is thus possible to prevent the generation of a large difference in the characteristics of the dark outputs between adjacent pixels of the two imaging apparatuses. This can reduce the possibility of image discontinuity occurring in the image data output from the two imaging apparatuses.

Figure 8A:
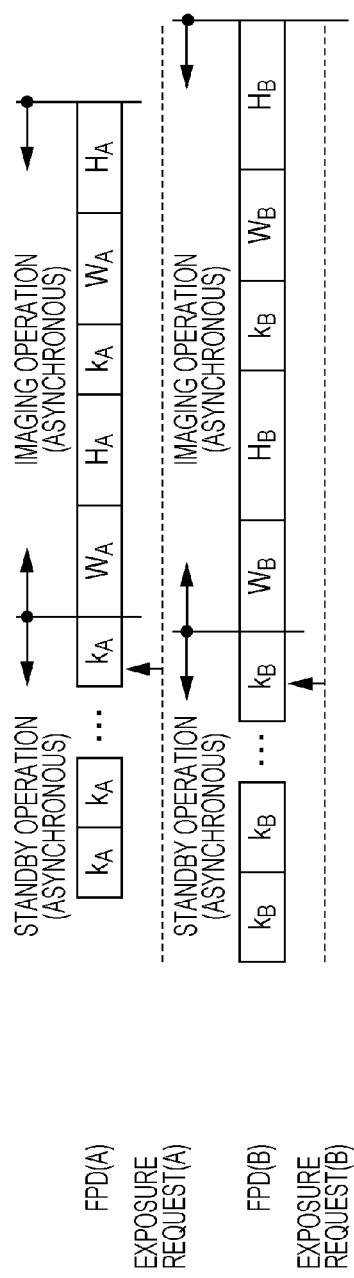
FIGS. 8A and 8B are timing charts illustrating operations performed by an imaging system according to the second embodiment of the present invention.
Figure 8B:
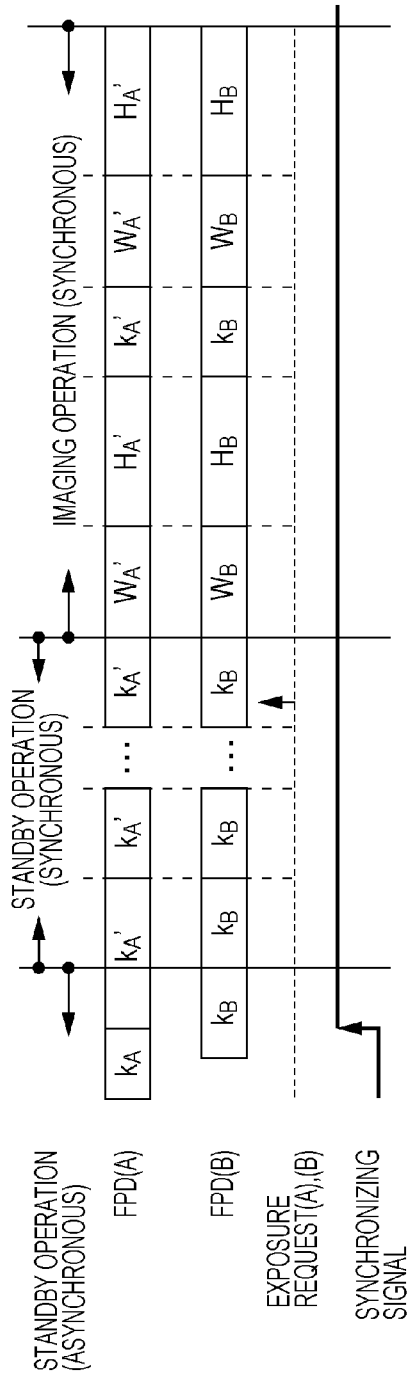

Operations of imaging apparatuses 701a and 701b in this embodiment are described below with reference to FIGS. 8A and 8B. In FIGS. 8A and 8B, the imaging apparatuses 701a and 701b use the same FPD. However, the scanning time for obtaining one image from the imaging apparatus 701b is different from that from the imaging apparatus 701a, and the two imaging apparatuses 701a and 701b are disposed in parallel. FIG. 8A is a timing chart illustrating the operations of the imaging apparatuses 701a and 701b in the asynchronous mode of this embodiment. FIG. 8B is a timing chart illustrating the operations of the imaging apparatuses 701a and 701b in the synchronous mode of this embodiment. Until receiving a control signal based on a radiation exposure request from the control computer, the controller controls the FPD to perform a standby operation including an initializing operation k that is repeatedly performed in a predetermined cycle. Then, upon receiving a control signal based on a radiation exposure request from the control computer, the controller performs an imaging operation including a storage operation W and an output operation H. In the still-image radiography, more preferably, the first storage operation W and output operation H is performed, followed by one initializing operation k, and then, the second storage operation W and output operation H is performed. By performing the first storage operation and output operation, radiation image data is obtained from the imaging apparatus, and by performing the second storage operation and output operation, image data for offset correction is obtained. Between the first storage operation and output operation and the second storage operation and output operation, at least one initializing operation k is performed in the same cycle as that of the initializing operation K performed before the first storage operation W and output operation H. This provides matching for the driving histories of the individual image data, which makes it possible to perform offset correction good enough to reduce shading. The initializing operation performed between two operations is not restricted to one time, and may be performed a plurality of times in the same cycle as that of the initializing operation k performed before the first storage operation W and output operation H.

In the asynchronous mode shown in FIG. 8A, the imaging apparatuses 701a and 701b independently perform operations. Accordingly, the start time, the length, and the number of repeating times of the operations are different between the FPD(A) and the FPD(B). If such operations are used in the synchronous mode, the time required for scanning and the scanning start time become different between the imaging apparatuses. This may cause image discontinuity, thereby giving rise to the deterioration of the image quality when performing image synthesizing.

Thus, in the synchronous mode according to the present invention, as shown in FIG. 8B, in accordance with a synchronization signal from the control computer, the controllers of the imaging apparatuses 701a and 701b control the FPD(A) and the FPD(B), respectively, so that the operations of the FPD(A) and the FPD(B) are synchronized with each other. In the first embodiment, the start time and the number of repeating times of each of the standby operation and the imaging operation of the FPD(A) are synchronized with those of the FPD(B). In this embodiment, in addition to this factor, the period of each operation of the FPD(A) is allowed to coincide with that of the FPD(B). In this case, the start time, the length, and the number of repeating times of the FPD(A) are preferably controlled based on the FPD(B) whose output operation H is longer than that of the FPD(A) in the asynchronous mode.

This embodiment includes a control operation for matching the time required for the scanning operation when different types of FPDs are used. Thus, in addition to the advantages offered by the first embodiment, the discontinuity of image data output from the plurality of imaging apparatuses shown in FIGS. 1A and 1B is further reduced, thereby making it possible to further suppress the deterioration of the image quality when image synthesizing is performed.

The individual embodiments of the present invention may be realized by executing a program by a computer contained in the controller 106 or the control computer 108 shown in FIGS. 1A and 1B. Also, means for supplying the program to the computer, for example, a computer-readable recording medium, such as a CD-ROM recording the program thereon, or a transmission medium, such as the Internet, for transmitting the program may be applied as an embodiment of the present invention. The above-described program may also be applied as an embodiment of the present invention. The above-described program, recording medium, transmission medium, and program product are included in the scope of the present invention. Also, an invention made by a combination that is easily conceivable by the first or second embodiment is also included in the scope of the present invention.

According to the invention of the present application, it is possible to provide an imaging system that includes a plurality of FPDs which can independently obtain images and which can be disposed as desired and that can prevent the deterioration of the image quality when performing image synthesizing.

While the present invention has been described with reference to exemplary embodiments, it is to be understood that the invention is not limited to the disclosed exemplary embodiments. In the present invention, examples of radiation include, not only α rays, β rays, γ rays, etc., which are beams of particles (including photons) emitted as a result of radioactive decay, but also beams having an energy equivalent to or higher than the above-described beams, for example, X rays, particle beams, cosmic rays, etc. The scope of the following claims is to be accorded the broadest interpretation so as to encompass all modifications and equivalent structures and functions.

This application claims the benefit of International Patent Application No. PCT/JP2010/058357, filed May 18, 2010, which is hereby incorporated by reference herein in its entirety.

The invention claimed is:

1. An imaging system comprising:
a plurality of imaging apparatuses, each of the imaging apparatuses including a detector for performing an imaging operation for outputting image data corresponding to applied radiation or light and a controller that controls the operation of the detector, and each of the imaging apparatuses independently performing an imaging operation and being movable in accordance with a relative positional relationship thereof;
sensing means that obtains information concerning the relative positional relationship of the imaging apparatuses; and
a control computer that determines operations of the imaging apparatuses by using the information obtained from the sensing means and that sends a control signal for performing the determined operations to the controller,
wherein, in a case where the relative positional relationship is a parallel arrangement in which the imaging apparatuses are disposed in parallel with respect to a scanning direction of each of the imaging apparatuses, the control computer determines the operations of the imaging apparatuses so that the scanning direction of each of the imaging apparatuses becomes the same, and,
wherein, in a case where the relative positional relationship is a serial arrangement in which the imaging apparatuses are disposed in series with respect to the scanning direction of each of the imaging apparatuses, the control computer determines the operations of the imaging apparatuses so that the scanning direction of each of the imaging apparatuses becomes opposite to each other and so that a time at which scanning is started or ended becomes the same for each of the imaging apparatuses.

2. The imaging system according to claim 1, wherein, in a case where the relative positional relationship is a parallel/displacement arrangement in which the imaging apparatuses are disposed in parallel with respect to the scanning direction of each of the imaging apparatuses and are displaced from each other in the scanning direction, the control computer determines the scanning directions of the imaging apparatuses so that the scanning directions of the imaging apparatuses become the same, and the control computer determines a time at which the scanning of the imaging apparatuses is started so that adjacent pixels between the imaging apparatuses in a region in which the detectors of the imaging apparatuses are partially overlapped with each other in the scanning direction are scanned at the same time.

3. The imaging system according to claim 1, wherein the control computer determines the operations of the imaging apparatuses so that a difference in dark output characteristics between adjacent pixels of the imaging apparatuses becomes equal to or lower than a level at which the difference in the dark output characteristics is buried in random noise of the detector of one of the imaging apparatuses.

4. The imaging system according to claim 1, wherein the control computer determines the operations of the imaging apparatuses so that, in the case of fluoroscopic imaging, a difference in dark output between adjacent pixels of the imaging apparatuses becomes equal to or lower than twice the magnitude of random noise of the detector of one of the imaging apparatuses, and so that, in the case of radiographic imaging, the difference in the dark output between the adjacent pixels of the imaging apparatuses becomes equal to or lower than the magnitude of random noise of the detector of one of the imaging apparatuses.

5. The imaging system according to claim 1, wherein, in a case where one of the imaging apparatuses which are disposed in parallel with respect to the scanning direction of each of the imaging apparatuses is different from the remaining imaging apparatus in at least one of the number of pixels and a pixel pitch and where a scanning time of the imaging apparatuses for obtaining one image is the same for the imaging apparatuses when the imaging apparatuses independently perform an imaging operation, or in a case where the scanning time of the imaging apparatuses for obtaining one image is different between the imaging apparatuses when the imaging apparatuses independently perform an imaging operation and where the number of pixels and the pixel pitch are the same for the imaging apparatuses, the control computer determines the operations of the imaging apparatuses so that the scanning directions of the imaging apparatuses become the same and that pixels most adjacent to each other between the imaging apparatuses are scanned at the same time.

6. The imaging system according to claim 1, wherein the sensing means includes a sensing unit provided for each of the imaging apparatuses or a sensing unit provided separately from each of the imaging apparatuses.

7. The imaging system according to claim 1, further comprising:
a mechanism for holding the detector; and
a function for driving the mechanism,
wherein the control computer determines positions to which the imaging apparatuses are moved by using the information, and moves the imaging apparatuses by using the mechanism and the function.

8. The imaging system according to claim 1, further comprising a display apparatus that displays information concerning the operations of the imaging apparatuses determined by the control computer.

9. The imaging system according to claim 1, wherein the detector includes:
- a detection unit in which a plurality of pixels are disposed in a matrix of rows and columns, each pixel having a conversion element for converting radiation or light into electric charge and a switch element for outputting an electric signal corresponding to the electric charge,
- a drive circuit that is connected to a plurality of drive lines disposed in the column direction, each of the plurality of drive lines being connected to a plurality of switch elements in the row direction, and
- a setting unit that can set the scanning direction, which is the order in which a drive signal is supplied to the plurality of drive lines, in two directions so as to drive the detection unit, and
- a readout circuit that is connected to a plurality of signal lines disposed in the row direction, each of the plurality of signal lines being connected to the plurality of switch elements in the column direction, so as to output the electric signal as image data from the detection unit which is driven in the scanning direction.

10. A control method for controlling an imaging system that includes a plurality of imaging apparatuses, each of imaging apparatuses including a detector for performing an imaging operation for outputting image data corresponding to applied radiation or light and a controller that controls the operation of the detector, each of the imaging apparatuses independently performing an imaging operation and being movable in accordance with a relative positional relationship thereof, the control method comprising:
- an obtaining step of obtaining information indicative of the relative positional relationship of the imaging apparatuses; and
- a determination step of determining operations of each of the imaging apparatuses by using the obtained information,
- wherein, in a case where the relative positional relationship is a parallel arrangement in which the imaging apparatuses are disposed in parallel with respect to a scanning direction of each of the imaging apparatuses, the determination step determines the operations of the imaging apparatuses so that the scanning direction of each of the imaging apparatuses becomes the same, and,
- wherein, in a case where the relative positional relationship is a serial arrangement in which the imaging apparatuses are disposed in series with respect to the scanning direction of each of the imaging apparatuses, the determination step determines the operations of the imaging apparatuses so that the scanning direction of each of the imaging apparatuses becomes opposite to each other and so that a time at which scanning is started or ended becomes the same for each of the imaging apparatuses.

11. The control method according to claim 10, wherein, in a case where the relative positional relationship is a parallel/displacement arrangement in which the imaging apparatuses are disposed in parallel with respect to the scanning direction of each of the imaging apparatuses and are displaced from each other in the scanning direction, the determination step determines the scanning direction of each of the imaging apparatuses so that the scanning direction of each of the imaging apparatuses becomes the same, and the determination step determines a time at which the scanning of the imaging apparatuses is started so that adjacent pixels between the imaging apparatuses in a region in which the detectors of the imaging apparatuses are partially overlapped with each other in the scanning direction are scanned at the same time.

12. The control method according to claim 10, wherein the determination step determines the operations of the imaging apparatuses so that a difference in dark output characteristics between adjacent pixels of the imaging apparatuses becomes equal to or lower than a level at which the difference in the dark output characteristics is buried in random noise of the detector of one of the imaging apparatuses.

13. The control method according to claim 10, wherein the determination step determines the operations of the imaging apparatuses so that, in the case of fluoroscopic imaging, a difference in dark output between adjacent pixels of the imaging apparatuses becomes equal to or lower than twice the magnitude of random noise of the detector of one of the imaging apparatuses, and so that, in the case of radiographic imaging, the difference in the dark output between the adjacent pixels of the imaging apparatuses becomes equal to or lower than random noise of the detector of one of the imaging apparatuses.

14. The control method according to claim 10, wherein, in a case where one of the imaging apparatuses which are disposed in parallel with respect to the scanning direction of each of the imaging apparatuses is different from the remaining imaging apparatus in at least one of the number of pixels and a pixel pitch and where a scanning time of the imaging apparatuses for obtaining one image is the same for the imaging apparatuses when the imaging apparatuses independently perform an imaging operation, or in a case where the scanning time of the imaging apparatuses for obtaining one image is different between the imaging apparatuses when the imaging apparatuses independently perform an imaging operation, and where the number of pixels and the pixel pitch are the same for the imaging apparatuses, the determination step determines the operations of the imaging apparatuses so that the scanning directions of the imaging apparatuses become the same and so that pixels most adjacent to each other between the imaging apparatuses are scanned at the same time.

15. The control method according to claim 10, wherein the imaging system further includes a mechanism for holding the detector, and a function for driving the mechanism, the control method further comprising:
- a determination step of determining positions to which the imaging apparatuses are moved by using the information; and
- a moving step of moving the imaging apparatuses on the basis of the determined positions by using the mechanism and the function.

16. The control method according to claim 10, further comprising a display step of displaying information concerning the determined operations of the imaging apparatuses.

17. The control method according to claim 10, wherein the detector includes: a detection unit in which a plurality of pixels are disposed in a matrix of rows and columns, each pixel having a conversion element for converting radiation or light into electric charge and a switch element for outputting an electric signal corresponding to the electric charge; a drive circuit that is connected to a plurality of drive lines disposed in the column direction, each of the plurality of drive lines being connected to a plurality of switch elements in the row direction; and a readout circuit that is connected to a plurality of signal lines disposed in the row direction, each of the plurality of signal lines being connected to the plurality of switch elements in the column direction, and wherein the control method further comprises:

a setting step of setting the scanning direction, which is the order in which a drive signal is supplied to the plurality of drive lines, in two directions so as to drive the detection unit;

a readout step of reading out the electric signal as image data from the detection unit which is driven in the scanning direction.

18. An imaging system comprising:

a plurality of imaging apparatuses, each of the imaging apparatuses including a detector in which a plurality of pixels for converting radiation or light into a charge is arranged in a matrix form, the plurality of pixels being serially scanned in a column direction on a row-by-row basis so as to output image data based on an electric signal, a scanning direction in which the plurality of pixels is scanned being settable to both directions, and a controller configured to control an operation of the detector, each of the plurality of imaging apparatuses independently performing an imaging operation and being movable in accordance with a relative positional relationship thereof;

sensing means for obtaining information concerning the relative positional relationship of the imaging apparatuses; and a control computer configured to determine the scanning direction of the plurality of imaging apparatuses, using the information obtained from the sensing means so that discontinuity of the image data output from the plurality of imaging apparatus is reduced, and to send a control signal for scanning the plurality of imaging apparatuses in the determined direction to the controller.

* * * * *